US008871784B2

(12) United States Patent
Moriconi et al.

(10) Patent No.: US 8,871,784 B2
(45) Date of Patent: Oct. 28, 2014

(54) 2-ARYL-ACETIC ACIDS, THEIR DERIVATIVES AND PHARMACEUTICAL COMPOSITIONS CONTAINING THEM

(75) Inventors: Alessio Moriconi, L'Aquila (IT); Marcello Allegretti, L'Aquila (IT); Maria Candida Cesta, L'Aquila (IT); Riccardo Bertini, L'Aquila (IT); Cinzia Bizzarri, L'Aquila (IT); Francesco Colotta, L'Aquila (IT)

(73) Assignee: Dompe'S.p.A., L'Aquila (IT)

( * ) Notice: Subject to any disclaimer, the term of this patent is extended or adjusted under 35 U.S.C. 154(b) by 0 days.

(21) Appl. No.: 12/828,181

(22) Filed: Jun. 30, 2010

(65) Prior Publication Data

US 2010/0267726 A1 Oct. 21, 2010

Related U.S. Application Data

(63) Continuation of application No. 10/541,429, filed as application No. PCT/EP2004/001021 on Feb. 4, 2004, now Pat. No. 7,776,909.

(30) Foreign Application Priority Data

Feb. 6, 2003 (EP) .................................... 03002716

(51) Int. Cl.

| A61K 31/192 | (2006.01) |
|---|---|
| A61K 31/40 | (2006.01) |
| A61K 31/405 | (2006.01) |
| A61K 31/407 | (2006.01) |
| C07D 209/26 | (2006.01) |
| C07C 311/09 | (2006.01) |
| C07C 57/58 | (2006.01) |
| C07D 209/42 | (2006.01) |
| C07C 311/21 | (2006.01) |
| C07D 471/04 | (2006.01) |
| C07D 295/13 | (2006.01) |
| C07D 207/337 | (2006.01) |
| C07C 57/30 | (2006.01) |
| C07C 311/51 | (2006.01) |

(52) U.S. Cl.
CPC .......... *C07D 207/337* (2013.01); *C07D 209/26* (2013.01); *C07C 311/09* (2013.01); *C07C 57/58* (2013.01); *C07D 209/42* (2013.01); *C07C 311/21* (2013.01); *C07D 471/04* (2013.01); *C07D 295/13* (2013.01); *C07C 57/30* (2013.01); *C07C 311/51* (2013.01)
USPC ............ 514/300; 514/412; 514/423; 514/568

(58) Field of Classification Search
USPC .................. 514/300, 412, 423, 568
See application file for complete search history.

(56) References Cited

U.S. PATENT DOCUMENTS

| 2,425,721 A | 8/1947 | Blicke et al. |
|---|---|---|
| 3,629,284 A | 12/1971 | Yamamoto et al. |
| 3,752,826 A | 8/1973 | Carson |
| 3,810,906 A * | 5/1974 | Yamamoto et al. ........... 546/324 |
| 3,833,608 A | 9/1974 | Rooney et al. |
| 3,883,541 A | 5/1975 | Hamilton |
| 7,135,495 B2 | 11/2006 | Torisu et al. |
| 7,291,644 B2 | 11/2007 | Torisu et al. |

FOREIGN PATENT DOCUMENTS

| FR | 1 574 570 A | 7/1969 |
|---|---|---|
| WO | WO 0010610 A2 * | 3/2000 |
| WO | WO-01/36415 A1 | 5/2001 |
| WO | WO-01/58852 A2 | 8/2001 |
| WO | WO-02/068377 A1 | 9/2002 |
| WO | WO 03/013526 A1 | 2/2003 |

OTHER PUBLICATIONS

Wong et al. The Journal of Pharmacology and Experimental Therapeutics 1973, 185(1), 127-138.*
Dormond et al. Drug Resistance Updates 2001, 4, 314-321.*
Hixson et al. Cancer Epidemiology, Biomarkers & Prevention 1994, 3, 433-438.*
Schafer et al. (Drug Discovery Today 2008, 13 (21/22), 913-916).*
Horig et al. Journal of Translational Medicine 2004, 2(44).*
Stedman's Medical Dictionary (26th ed. 1995) 1425, 1439.*
Stedman's Medical Dictionary (26th ed. 1995) 894.*
Brancaccio et al., Journal of Medicinal Chmeistry, American Chemical Society, Washington, U.S., vol. 24, 1981, pp. 998-1000.
Walsh et al., Journal of Medicinal Chemistry, vol. 25, No. 4, 1982, pp. 446-451.
K. Xie Cytokine and Growth Factor Reviews 2001, 12, 375-391.
Yang et al. Journal of Leukocyte Biology 1999, 66, 401-410.
Communication Pursuant to Article 94(3) EPC, Application 04 707 926.4, Dated Sep. 23, 2009.
Examiner's First Report on Patent Application No. 2004210082, IP Australia, dated Jun. 15, 2009.

(Continued)

*Primary Examiner* — Shawquia Young
(74) *Attorney, Agent, or Firm* — Steinfl & Bruno, LLP

(57) ABSTRACT

Selected 2-arylacetic acids, their derivatives and pharmaceutical compositions that contain these compounds are useful in inhibiting chemotactic activation of neutrophils (PMN leukocytes) induced by the interaction of Interleukin-8 (IL-8) with CXCR1 and CXCR2 membrane receptors. The compounds are used for the prevention and treatment of pathologies deriving from their activation. In particular, 2(ortho)-substituted arylacetic acids or their derivatives, such as amides and sulfonamides, lack cyclo-oxygenase inhibition activity and are particularly useful in the treatment of neutrophil-dependent pathologies such as psoriasis, ulcerative colitis, melanoma, chronic obstructive pulmonary disease (COPD), bullous pemphigoid, rheumatoid arthritis, idiopathic fibrosis, glomerulonephritis and in the prevention and treatment of damages caused by ischemia and reperfusion.

4 Claims, 2 Drawing Sheets

(56) References Cited

OTHER PUBLICATIONS

"Reperfusion Injury" Wikipedia article. accessed Oct. 24, 2008. http://en/wikipedia.org/wiki/Reperfusion_injury.

Gronowitz et al., "Some Substitution Reactions of 5-(2'Thienyl)pyrimidine and 5-(3'-Thienyl)pyrimidine," Chemica Scripta, vol. 13 (1), pp. 39-45, 1978-1979.

Jackson et al. "Preparation and Diels-Alder Reactivity of Thieno[2,3-c]-and Thieno[3,2-c]-pyran-3-ones, Stable 2,3-Dimethylenethiophene Derivatives; Synthesis of Benzothiophenes," J. Chem. Soc. Perkin Trans., pp. 2909-2918, 1990.

Quesnelle et al., "Sordaricin Antifungal Agents," Bioorganic & Medicinal Chemistry Letters, vol. 13, pp. 519-524, 2003.

Edgar et al., "Synthesis of L-(5-Chloro-2-pyridyl)glycine," J. Org. Chem., vol. 44, No. 3, 1979.

Jones et al., "Triazolopyridines. 18.1 Nucleophilic Substitution Reactions on Triazolopyridines; A New Route to 2,2'-Bipyridines," Teirahedron, vol. 53, No. 24, pp. 8257-8268, 1997.

Buu-Hoi et al., "Side Chain Bromination of Some Alkylna/phthalenes with N-Bromosuccinimide," Ecole Polytechnique, Paris, 1946.

Alam et al., "A Facile Synthesis of Phenylacetic Acids via Willgerodt-Kindler Reaction Under PTC Condition," Synthetic Communications, vol. 33, No. 1, pp. 59-63, 2003.

Brown et al., "Simple Pyrimidines. XVI A Synthetic Route to Some 2-9Pyrimidin-2'-yl)acetic Acids and Esters," Aust. J. Chem., 30, pp. 621-627, 1977.

\* cited by examiner

2-ARYL-ACETIC ACIDS, THEIR DERIVATIVES AND PHARMACEUTICAL COMPOSITIONS CONTAINING THEM

This application is a Continuation of copending U.S. application Ser. No. 10/541,429, filed on Jul. 5, 2005, which is the National Phase under 37 C.F.R. §371 of PCT International Application No. PCT/EP2004/001021 filed on Feb. 4, 2004, which designated the United States, and priority to both applications is claimed under 35 U.S.C. §120. This application also claims priority under 35 U.S.C. §119(a) to Patent Application Nos. 03002716.3 filed in the European Patent Office on Feb. 6, 2003.

BRIEF DESCRIPTION OF THE INVENTION

The present invention relates to 2-arylacetic acids and derivatives thereof, and to pharmaceutical compositions containing them, which are used in the prevention and treatment of tissue damage due to the exacerbated recruitment of polymorphonucleated neutrophils (PMN leukocytes) at inflammation sites. In particular, the invention is directed to 2-phenylacetic acids and derivatives thereof for the treatment of IL-8 mediated diseases, such as psoriasis, ulcerative colitis, COPD and of the damages caused by ischemia and reperfusion.

BACKGROUND OF THE INVENTION

Particular blood cells (macrophages, granulocytes, neutrophils, polymorphonucleated) respond to a chemical stimulus (when stimulated by substances called chemokines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including Interleukin-8 (IL-8, also referred to as CXCL8). Interleukin-8 is an endogenous chemotactic factor produced by most nucleated cells such as fibroblasts and macrophages.

In some pathological conditions, marked by exacerbated recruitment of neutrophils, a more severe tissue damage at the site is associated with the infiltration of neutrophilic cells. Recently, the role of neutrophilic activation in the determination of damage associated with post ischemia reperfusion and pulmonary hyperoxia was widely demonstrated.

The biological activity of IL-8 is mediated by the interaction of the interleukin with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995). Selective ligand are known which can distinguish between CXCR1 and CXCR2: GRO-α is an example of a CXCR2 selective chemotactic factor.

Potential pathogenic role of IL-8 in pulmonary diseases (lung injury, acute respiratory distress syndrome, asthma, chronic lung inflammation, and cystic fibrosis) and, specifically, in the pathogenesis of COPD (chronic obstructive pulmonary disease) through the CXCR2 receptor pathway has been widely described (D. W P Hay and H. M. Sarau., Current Opinion in Pharmacology 2001, 1:242-247).

Characteristic neutrophil accumulation occurs in acute and chronic pathologic conditions, for example in the highly inflamed and therapeutically recalcitrant areas of psoriatic lesions. Neutrophils are chemotactically attracted and activated by the sinergistic action of chemokines, IL-8 and Gro-a released by the stimulated keratinocytes, as well as of the C5a/C5a-desArg fraction produced via the alternative complement pathway activation (T. Terui et al., Exp. Dermatol., 9, 1, 2000).

Novel classes of potent and selective inhibitors of IL-8 biological activities (R-2-arylpropionic acid amides and N-acylsulfonamides) have been described as effective inhibitors of IL-8 induced neutrophils chemotaxis and degranulation (WO 01/58852; WO 00/24710). Furthermore, novel subclasses of R and S 2-phenylpropionic acids have been described (WO 03/043625) as potent IL-8 inhibitors completely lacking the undesired cyclo-oxygenase enzyme (COX) inhibitory effect. The inhibition of prostaglandin synthesis deriving from COX inhibition involves, in fact, an increase of cytokine production which results in the amplification of the undesired pro-inflammatory effects of neutrophils.

DETAILED DESCRIPTION OF THE INVENTION

Medicinal Chemistry studies have shown the crucial role of the methyl group on the propionic chain of 2-arylpropionic acids in order for them to exert their IL-8 inhibitory activity.

We have, in fact, found that 2-[4-isobutylphenyl]acetic acid (ibufenac) and 2-[3-benzoylphenyl]acetic acid (ketofenac), well known COX inhibitors belonging to the family of phenylacetic acids, do not exert any IL-8 inhibitory activity which is present, instead, in the potent corresponding phenylpropionic acids, such as ibuprofen and ketoprofen.

In general, 2-phenylacetic acids and their derivatives, such as amides and sulfonamides, lack any IL-8 inhibitory activity and this confirms the crucial role of the methyl group in the corresponding 2-phenylpropionic derivatives.

We have completed SAR studies on the different classes of 2-arylpropionic acids and derivatives described above, which allowed to exactly clarify the pharmacophore structure shared by all these novel classes of IL-8 inhibitors.

A pharmacophore is defined as the ensemble of steric and electronic requirements, in a class of biologically active compounds, necessary to ensure the biological activity; in general, the pharmacophore can be considered the ensemble of steric and electronic requirements necessary to ensure positive interactions between a biologically active molecule and its target. The assumption, in a pharmacophore study, is that all compounds in a training set share the same mechanism and interact with the same biological target.

We have now defined two pharmacophore models: a first model accounting for the biological activity of IL-8 inhibitors selectively acting on CXCR1 mediated pathway (hereinafter CXCR1 inhibitors), and a second model representing the sterile and electronic requirements of the IL-8 inhibitors dually acting on CXCR1 and CXCR2 mediated pathway (hereinafter CXCR1/CXCR2 inhibitors). These two models account for the observed Structure Activity Relationships since all the inactive molecules tested against the two complete pharmacophore hypothesis either miss crucial features superimposition (unfit) or fit the pharmacophore hypothesis in a high energy conformations. The two newly found pharmacophore models share four out of respectively five and six features; these four features are completely superimposable in the 3D chemical space. An outline of the common portion of the pharmacophore models is illustrated in FIG. 1.

Figure 1:
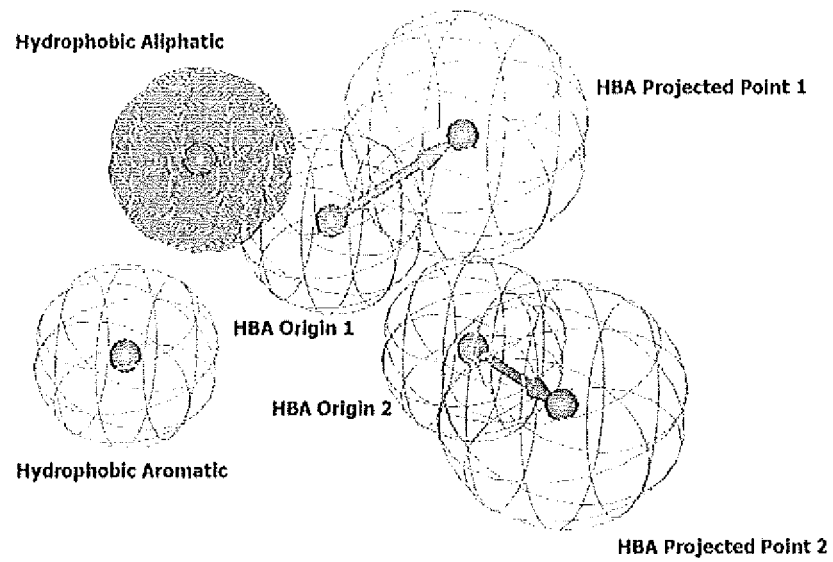
FIG. 1 graphically shows the four common features of the pharmacophores of respectively CXCR1 inhibitors and CXCR1/CXCR2 inhibitors. The following features types take part in the pharmacophore portion: two Hydrogen Bond Acceptors, one Hydrophobic Aromatic and one Hydrophobic Aliphatic. The (aromatic and aliphatic) hydrophobic features are represented by spheres of 1.7 Angstroms radius. The hydrogen bond acceptor is represented by a vector function consisting two spheres whose centroids are 3.0 Angstroms apart. The smaller (1.7 Angstroms radius) sphere defines the position of the hydrogen bond acceptor atom on the ligand and the larger sphere (2.3 Angstroms) defines the projected point of the hydrogen bond acceptor from the receptor site. The solid sphere represents the exact location in the 3D space of the methyl group of the phenylpropionic moiety.

Pharmacophore generation has been performed using the Catalyst™ software, version 4.7 (Molecular Simulations, Inc., San Diego, Calif.), which is designed to identify common configurations of the active molecules by means of their chemical features. A configuration is a set of relative locations in 3D space, each associated with a feature type. All the compounds in the training set were described in terms of their chemical functions associated within the 3D space. Furthermore, each chemical moiety can be considered by the software as more than one feature on the basis of the found similarity. For example, an aromatic ring can "establish" both hydrophobic interactions and π-π interactions in the target site and this different behaviour is referred to different features (Hydrophobic, Hydrophobic aromatic).

A functional group in a molecule can be associated to more than one feature, depending on its chemical and phisical properties, and different functional groups can show behaviour similarity in the interaction with the target so mapping the same feature.

Analysis of the feature definitions and selection of the features is a crucial step in the pharmacophore hypothesis generation. It is well known that the most important forces involved in molecular recognition are represented by electrostatic interactions, hydrogen bonding and hydrophobic interactions. We adopted several features definitions relating the chemical nature of the group to the ability of engaging specific interactions responsible for the biological activity.

Features Definitions

Hydrogen Bond Acceptor (HBA) (Lipid)

A Hydrogen bond acceptor lipid feature matches the following types of atoms or groups of atoms which are surface accessibility: nitrogens, oxygens, or sulphurs (except hypervalent) that have a lone pair and charge less than or equal to zero. Since a lipid environment was considered, all basic amines (primary, secondary and tertiary) are included in this definition. The hydrogen bond is a highly directional interaction, this feature is so indirectly linked to the theoric position of the corresponding hydrogen donor. Three hydrogen bonds positions are for instance considered on carbonyl group (acceptor), the first two along the ideal positions of the lone pairs and a third one along the C=O bond direction.

Hydrophobic (Aliphatic, Aromatic)

Hydrophobic feature is defined as a contiguous set of atoms that are not adjacent to any concentrations of charge (charged atoms or electronegative atoms), in a conformer such that the atoms have surface accessibility, including phenyl, cycloalkyl, isopropyl, and methyl.

Nevertheless it has been necessary to distinguish the aromatic hydrophobic feature from the aliphatic one in order to grant a good fitting with biological results. The former considers only the aromatic atoms, the latter considers only the aliphatic atoms.

A molecule is considered matching a configuration only if possesses a set of relative features and specific conformation such that its features can be superimposed with the corresponding "ideal" locations. A set of features can be considered superimposed if each feature lies within a specific distance on tolerance, from the ideal point.

The absolute sphere centroids co-ordinates of each feature are listed below:

HYDROPHOBIC AROMATIC has Cartesian co-ordinates +2.588, +0.613, −1.940 respectively along XYZ axes.

HYDROPHOBIC ALIFATIC has Cartesian co-ordinates of +1.788, +2.693, +1.260 respectively along XYZ axes.

HYDROGEN BOND ACCEPTOR PROJECTED POINT 1 has Cartesian co-ordinates of −2.713, +2.333, +2.840 respectively along XYZ axes.

HYDROGEN BOND ACCEPTOR ORIGIN 1 has Cartesian co-ordinates of −0.233, +0.936, +1.877 respectively along XYZ axes.

HYDROGEN BOND PROJECTED ACCEPTOR POINT 2 (optional) has Cartesian co-ordinates of −5.013, −1.188, −0.400 respectively along XYZ axes.

HYDROGEN BOND ACCEPTOR ORIGIN 2 (optional) has Cartesian co-ordinates of −2.688, −1.514, +1.472 respectively along XYZ axes.

Mapping of the first three features (HYDROPHOBIC ALIPHATIC, HYDROPHOBIC AROMATIC, HYDROGEN BOND ACCEPTOR 1) is crucial for the biological IL-8 inhibitory activity of the class; the fourth feature (HYDROGEN BOND ACCEPTOR 2) can be optionally mapped by the molecules of the class but the presence of the second hydrogen bond acceptor group is not indispensable.

Tolerances on all the distances between the chemical features have been established in +0.5 Angstroms and tolerances on the geometric angles ±20 degrees.

As previously discussed, other pharmacophore points are required in order to complete the pharmacophore analysis but their description is not relevant for the purposes of present invention. The observed CXCR1/CXCR2 selectivity in the class is strictly related to the ability of the inhibitors to match specific points in the non-common part of the pharmacophore.

Figure 2:
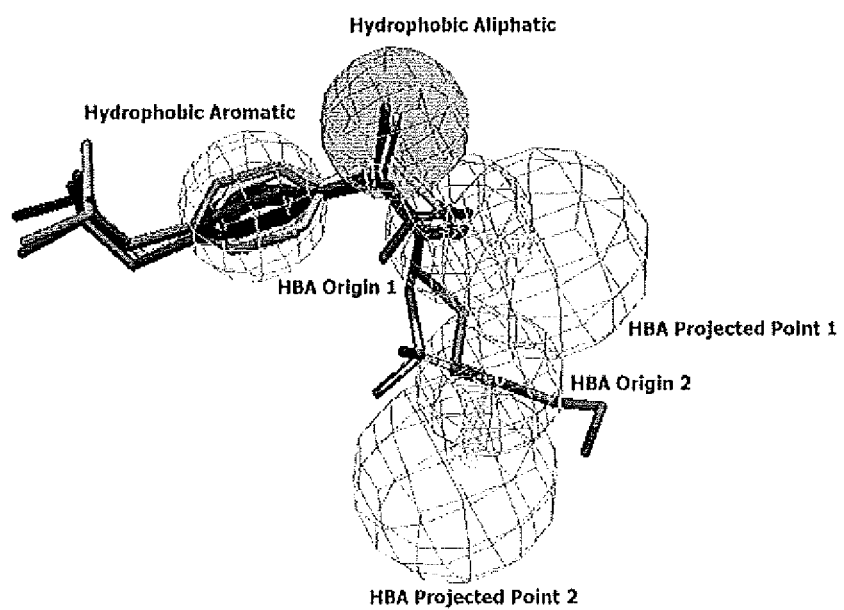
FIG. 2 illustrates superimposition of the following Arylpropionic derivatives: R(−) 2-(4-isobutylphenyl) propionic acid; R(−)-2-(4-isobutylphenyl)propionyl methanesulphonamide; R(−)-N-(2'-hydroxyethoxyethyl)-2-(4-isobutylphenyl) propionamide. The solid sphere represents the exact location in the 3D space of the methyl group of the phenylpropionic moiety.

On the contrary, as far as the common part of the pharmacophore is concerned, a general superimposition mode is observed for CXCR1 inhibitors and CXCR1/CXCR2 inhibitors belonging to the classes of 2-phenylpropionic acids, 2-phenylpropionyl sulphonamides and 2-phenylpropionamides as outlined in FIG. 2. The solid sphere represents the exact location in the 3D space of the methyl group of the phenylpropionic moiety.

In the retrieved ligands which partially or fully map this hypothesis (FIG. 2) the phenyl residue of the 2-phenylpropionic chemical structure always matches very well the HYDROPHOBIC AROMATIC feature; the HYDROGEN BOND ACCEPTOR (HBA) 1 feature is consistently well matched by the carbonylic oxygen of the propionyl residue; the HYDROGEN BOND ACCEPTOR (HBA) 2 feature can be optionally matched by a second Hydrogen Bond Acceptor atom on the residue linked at the amidic or sulphonamidic nitrogen; the HYDROPHOBIC ALIPHATIC feature is invariably matched by the methyl group of the propionyl residue. Phenylacetic acids and derivatives, on the basis of the above considerations, obviously fail to match the pharmacophore hypothesis, since the crucial HYDROPHOBIC ALIPHATIC feature, represented by the solid sphere in FIG. 2, is missing in their chemical structure.

We have now found out that selected subclasses of 2-arylacetic acids and derivatives thereof, which lack the methyl group of the propionyl residue, show the surprising ability to effectively inhibit IL-8 induced neutrophils chemotaxis and degranulation.

The present invention thus provides use of 2-arylacetic acid compounds and derivatives of formula (I):

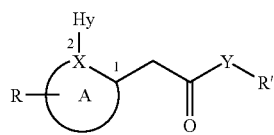

and pharmaceutically acceptable salts thereof,
wherein
A includes the X atom and represents a 5-6 membered aromatic or heteroaromatic ring optionally including a heteroatom, or a further heteroatom when X is N, selected from N (nitrogen), O (oxygen), S (sulfur); the 5-6 membered aromatic or heteroaromatic ring is optionally fused with a second ring to give bicyclic aromatic or heteroaromatic structures;
labels 1 and 2 mark the relevant positions on the A ring;
the X atom is selected from N (nitrogen) and C (carbon);
R is a substituting group on the A ring selected from:
  a group in the 3 (meta) position selected from a linear or branched $C_1$-$C_5$ alkyl, $C_2$-$C_5$-alkenyl or $C_2$-$C_5$-alkynyl group, substituted or not-substituted phenyl, linear or branched $C_1$-$C_5$ hydroxyalkyl, $C_2$-$C_5$-acyl, substituted or not-substituted benzoyl;
  a group in the 4 (para) position selected from $C_1$-$C_5$ alkyl, $C_2$-$C_5$-alkenyl or $C_2$-$C_5$-alkynyl group, $C_3$-$C_6$-cycloalkyl, $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, 2-furyl; 3-tetrahydrofuryl; 2 thiophenyl; 2-tetrahydrothiophenyl groups or a $C_1$-$C_8$-alkanoyl, cycloalkanoyl or arylalkanoyl-$C_1$-$C_5$-alkylamino group;
Hy is a small hydrophobic group with a steric hindrance factor ν ranging between 0.5 and 0.9 Å (where ν is the Charton steric constant for substituents), including methyl, ethyl, chlorine, bromine, methoxy, trifluoromethyl;
The Y group is selected from O (oxygen) and NH;
when Y is O (oxygen), R' is H (hydrogen);
When Y is NH, R' is selected from
  —H, $C_1$-$C_5$-alkyl, $C_1$-$C_5$-cycloalkyl, $C_1$-$C_5$-alkenyl;
  an amino acid residue consisting of straight or branched $C_1$-$C_6$-alkyl, $C_1$-$C_6$-cycloalkyl, $C_1$-$C_6$-alkenyl, phenylalkyl substituted with one or more carboxy (COOH) groups;
  an amino acid residue consisting of straight or branched $C_1$-$C_6$-alkyl, $C_1$-$C_6$-cycloalkyl, $C_1$-$C_6$-alkenyl, phenylalkyl, bearing along the chain a heteroatom selected from oxygen and sulfur and with one or more carboxy (COOH) groups;
  a residue of formula —$CH_2$—$CH_2$—Z—($CH_2$—$CH_2$O)nR" wherein R" is H or $C_1$-$C_5$-alkyl, n is an integer from 0 to 2 and Z is oxygen or sulfur;
  a residue of formula —($CH_2$)n-NRaRb wherein n is an integer from 0 to 5 and each Ra and Rb, which may be the same or different, are $C_1$-$C_6$-alkyl, $C_1$-$C_6$-alkenyl or, alternatively, Ra and Rb, together with the nitrogen atom to which they are bound, form a heterocycle from 3 to 7 members of formula (II)

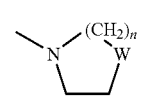

wherein W represents a single bond, $CH_2$, O, S or N—Rc, wherein Rc is H, $C_1$-$C_6$-alkyl or $C_1$-$C_6$-alkylphenyl;
a residue OR" wherein R" is H, methyl, carboxymethyl;
a residue of formula $SO_2$Rd wherein Rd is $C_1$-$C_6$-alkyl, $C_1$-$C_6$-cycloalkyl, $C_1$-$C_6$-alkenyl;
in the preparation of a medicament for the inhibition of IL-8 induced human PMNs chemotaxis.

The aromatic ring in the A group may be optionally substituted with further groups such as $C_1$-$C_5$-alkyl or a halogen group.

The term "substituted" in the above definition means substituted with a group selected from $C_1$-$C_5$-alkyl, halogen, hydroxy, $C_1$-$C_5$-alkoxy, amino, $C_1$-$C_5$-alkylamino, nitro, or a cyano group.

Preferred A groups in compounds of formula (I) are aromatic or heteroaromatic rings selected from benzene, naphthalene, pyridine, pyrimidine, pyrrole, imidazole, furane, thiophene, indole and 7-aza-indole.

Preferred compounds of formula (I) are those wherein the group YR' is OH; preferred R' groups when Y is NH are:
  the amino acid residue of glycine, β-alanine, γ-aminobutyric acid or residues of an L-α-amino acid selected in the group of L-alanine, valine, leucine, isoleucine, norleucine, phenylalanine, S-methylcysteine, methionine;
  a residue of formula —$CH_2$—$CH_2$—O—($CH_2$—$CH_2$O)R" wherein R" is H or $C_1$-$C_5$-alkyl;
  a residue of formula —(CH2)n-NRaRb wherein n is an integer from 2 to three, more preferably 3 and the group NRaRb is N,N-dimethylamine, N,N-diethylamine, 1-piperidyl, 4-morpholyl, 1-pyrrolidyl, 1-piperazinyl, 1-(4-methyl)piperazinyl;
  a residue OR' wherein R' is H, methyl;
a residue of formula $SO_2$Rd wherein Rd is methyl, ethyl or isopropyl.

Preferred R groups in compounds of formula (I) are 3'-benzoyl, 3'-(4-chloro-benzoyl), 3'-(4-methyl-benzoyl), 3'-acetyl, 3'-propionyl, 3'-isobutanoyl, 3'-ethyl, 3'-isopropyl, 4'-isobutyl, 4'-trifluoromethanesulphonyloxy, 4'-benzenesulphonyloxy, 4'-trifluoromethanesulphonylamino, 4'-benzenesulphonylamino, 4'-benzenesulphonylmethyl, 4'-acetyloxy, 4'-propionyloxy, 4'-benzoyloxy, 4'-acetylamino, 4'-propionylamino, 4'-benzoylamino.

Preferred Hy groups in compounds of formula (I) are methyl, ethyl, chlorine, bromine, methoxy, trifluoromethyl.

Particularly preferred is the use of compounds selected from:
(3-benzoyl-2-methylphenyl)acetic acid
(2-chloro-3-propionylphenyl)acetic acid
(3-isopropyl-2-methylphenyl)acetic acid
(4-isobutyl-2-methylphenyl)acetic acid
{2-methyl-4-[(phenylsulphonyl)amino]phenyl}acetic acid
{2-methyl-4-[(trifluoromethanesulphonyl)amino]phenyl}acetic acid
{2-chloro-4-[(trifluoromethanesulphonyl)oxy]phenyl}acetic acid
(5-acetyl-1-methyl-1H-pyrrol-2-yl)acetic acid
[1-methyl-5-(4-methylbenzoyl)-1H-pyrrol-2-yl]acetic acid
(5-benzoyl-1-methyl-1H-pyrrol-2-yl)acetic acid
[1-methyl-5-(4-chlorobenzoyl)-1H-pyrrol-2-yl]acetic acid
(5-isobutyryl-1-methyl-1H-pyrrol-2-yl)acetic acid
(1-benzoyl-2-methyl-1H-pyrrol-3-yl)acetic acid
(1-benzoyl-2-chloro-1H-pyrrol-3-yl)acetic acid
(1-benzoyl-2-methyl-1H-indol-3-yl)acetic acid
[1-(4-chlorobenzoyl)-2-methyl-1H-indol-3-yl]acetic acid
(1-isopropyl-2-methyl-1H-pyrrole[2,3-b]pyridin-3-yl)acetic acid
(3-benzoyl-2-methoxyphenyl)acetic acid
(5-acetyl-1-methyl-1H-pyrrol-2-yl)acetamide
(5-acetyl-1-methyl-1H-pyrrol-2-yl)-N-carboxymethylacetamide
(S)(5-acetyl-1-methyl-1H-pyrrol-2-yl)-N-(2-carboxyethyl)acetamide
(5-acetyl-1-methyl-1H-pyrrol-2-yl)-N-(3-dimethylaminopropyl)acetamide
(S)(5-acetyl-1-methyl-1H-pyrrol-2-yl)-N-(1-carboxy-2-methoxyethyl)acetamide
(4-isobutyl-2-methylphenyl)acetamide
(2-chloro-3-propionylphenyl)-N-(3-dimethylaminoethyl)acetamide
(3-isopropyl-2-methylphenyl)-N-[3-(1-piperidinyl)propyl]acetamide
(3-benzoyl-2-methylphenyl)acetamide
(1-benzoyl-2-methyl-1H-indol-3-yl)acetamide
(1-benzoyl-2-methyl-1H-indol-3-yl)-N-(3-dimethylaminopropyl)acetamide
[1-(4-chlorobenzoyl)-2-methyl-1H-indol-3-yl]acetamide
[1-(4-chlorobenzoyl)-5-methoxy-2-methyl-1H-indol-3-yl]acetamide
{2-chloro-4-[(trifluoromethanesulphonyl)oxy]phenyl}-N-(2-hydroxyethoxyethyl)acetamide
(1-benzoyl-2-methyl-1H-pyrrol-3-yl)-N-(2-methoxyethyl)acetamide
(1-benzoyl-2-chloro-1H-pyrrol-3-yl)-N-[3-(1-morpholino)propyl]acetamide
(5-isobutyryl-1-methyl-1H-pyrrol-2-yl)acetamide
(5-benzoyl-1-methyl-1H-pyrrol-2-yl)-N-(2-carboxymethyl)acetamide
[1-methyl-5-(4-chlorobenzoyl)-1H-pyrrol-2-yl]-N-(2-hydroxyethoxyethyl)acetamide
[1-methyl-5-(4-chlorobenzoyl)-1H-pyrrol-2-yl]acetamide
{2-methyl-4-[(phenylsulphonyl)amino]phenyl}-N-(3-dimethylaminopropyl)acetamide
(3-benzoyl-2-methoxyphenyl)acetamide.

The present invention further provides novel 2-arylacetic acids and derivatives of formula (Ia),

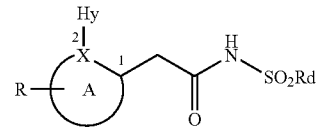

and pharmaceutically acceptable salts thereof,
wherein:
A includes the X atom and represents a 5-6 membered aromatic or heteroaromatic ring optionally including a heteroatom, or a further heteroatom when X is N, selected from N (nitrogen), O (oxygen), S (sulfur); the 5-6 membered aromatic or heteroaromatic ring is optionally fused with a second ring to give bicyclic aromatic or heteroaromatic structures;
labels 1 and 2 mark the relevant positions on the A ring;
the X atom is selected from N (nitrogen) and C (carbon);
R is a substituting group on the A ring selected from:
a group in the 3 (meta) position selected from a linear or branched $C_1$-$C_5$ alkyl, $C_2$-$C_5$-alkenyl or $C_2$-$C_5$-alkynyl group, substituted or not-substituted phenyl, linear or branched $C_1$-$C_5$ hydroxyalkyl, $C_2$-$C_5$-acyl, substituted or not-substituted benzoyl;
a group in the 4 (para) position selected from $C_1$-$C_5$ alkyl, $C_2$-$C_5$-alkenyl or $C_2$-$C_5$-alkynyl group, $C_3$-$C_6$-cycloalkyl, $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, 2-furyl; 3-tetrahydrofuryl; 2 thiophenyl; 2-tetrahydrothiophenyl groups or a $C_1$-$C_8$-alkanoyl, cycloalkanoyl or arylalkanoyl-$C_1$-$C_5$-alkylamino group, such as acetyl-N-methyl-amino, pivaloyl-N-ethyl-amino group;
Hy is a small hydrophobic group with a steric hindrance factor v ranging between 0.5 and 0.9 Å (where v is the Charton steric constant for substituents), including methyl, ethyl, chlorine, bromine, methoxy, trifluoromethyl;
wherein Rd is $C_1$-$C_6$-alkyl, $C_1$-$C_6$-cycloalkyl, $C_1$-$C_6$-alkenyl,
Preferred compounds of formula (Ia) are those wherein, A is benzene, pyridine, pyrimidine, pyrrole, imidazole, furane, thiophene, indole;
Rd is methyl, ethyl or isopropyl;
Hy is selected from methyl, ethyl, chlorine, bromine, methoxy, trifluoromethyl.
Particularly preferred compounds of the invention are:
(5-acetyl-1-methyl-1H-pyrrol-2-yl)acetyl methanesulphonamide
(4-isobutyl-2-methylphenyl)acetyl methanesulphonamide
{2-methyl-4-[(trifluoromethanesulphonyl)amino]phenyl}acetyl methanesulphonamide
[1-methyl-5-(4-methylbenzoyl)-1H-pyrrol-2-yl]acetyl-methanesulphonamide Compounds of formula (Ia) wherein Rd is above defined are prepared by transforming a compound of formula (I) wherein YR' is OH in a reactive intermediate such as an acylhalide, preferably an acyl chloride, or a known "active ester", preferably a benzotriazolyl ester, and reacting with a compound of formula $NH_2SO_2Rd$ in presence of a suitable base, preferably potassium tert-butoxide. The compounds of the invention, despite of the lack of the methyl group on the propionic chain, are potent and selective inhibitors of the human PMNs chemotaxis induced by IL-8.

As above discussed, molecules lacking the above methyl group on the chiral carbon atom of the propionic chain have been generally found inactive in the IL-8 induced chemotaxis assay, owing to the key role of the methyl group in mapping the HYDROPHOBIC ALIPHATIC feature of the pharmacophore.

Figure 3:
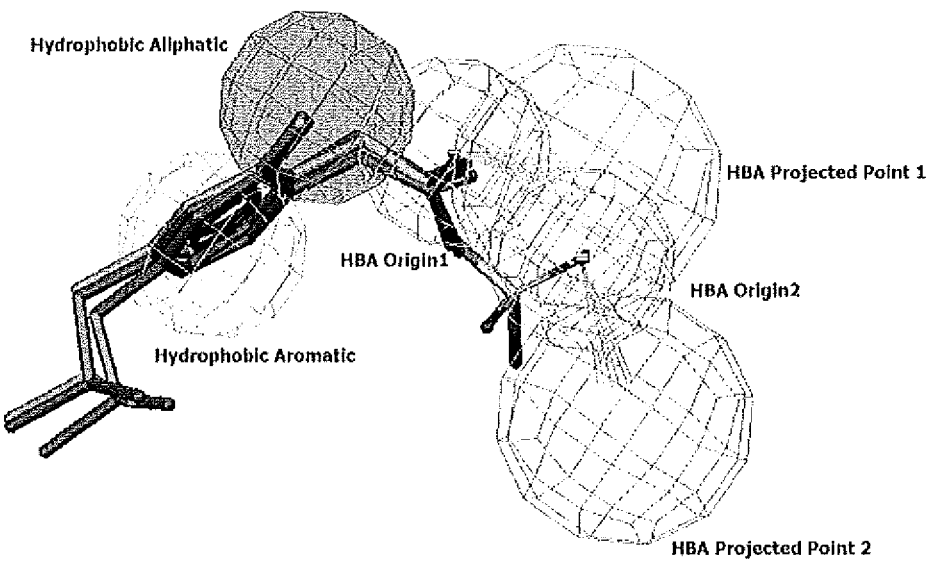
FIG. 3 illustrates superimposition of the following Arylacetic derivatives: (2-methyl-4-isobutylphenyl)acetic acid; (2-methyl-4-isobutylphenyl)acetyl methanesulphonamide; (2-methyl-4-isobutylphenyl)acetamide.
Figure 4:
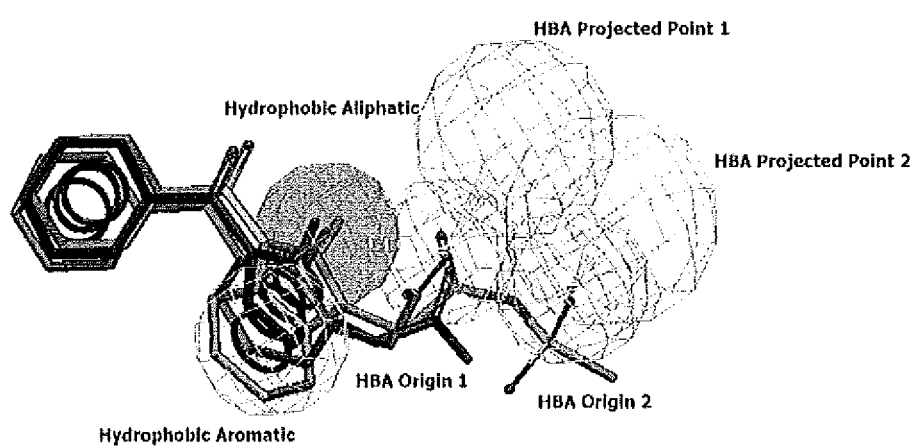
FIG. 4 illustrates superimposition of the following Arylacetic derivatives: (5-benzoyl-1-methyl-1H-pyrrol-2-yl) acetic acid; (1-benzoyl-2-methyl-1H-indol-3-yl)acetyl methanesulphonamide; (2-chloro-3-benzoylphenyl)acetamide.

The general superimposition mode of the compounds of the invention to the pharmacophore hypothesis described above and outlined in FIG. 1, is illustrated in FIGS. 3 and 4.

FIG. 3 illustrates superimposition of the following compounds belonging to the class of arylacetic derivatives: (2-methyl-4-isobutylphenyl)acetic acid; (2-methyl-4-isobutylphenyl)acetyl methanesulphonamide; (2-methyl-4-isobutylphenyl)acetamide.

FIG. 4 illustrates superimposition of the following compounds belonging to the class of arylacetic derivatives: (5-benzoyl-1-methyl-1H-pyrrol-2-yl)acetic acid; (1-benzoyl-2-methyl-1H-indol-3-yl)acetyl methanesulphonamide; (2-chloro-3-benzoylphenyl)acetamide.

The compounds of the invention derive their strong biological activity from the unexpected property of the Hydrophobic group (Hy) in the 2 position (Formula I) to correctly match the HYDROPHOBIC ALIPHATIC feature of the pharmacophore model represented by the solid spheres in FIGS. 3 and 4. A general pharmacophore superimposition mode is observed indeed for the compounds of formula (I). The Hydrophobic group (Hy) of the retrieved ligands which partially or fully map this hypothesis invariably matches the HYDROPHOBIC ALIPHATIC to feature (solid sphere, FIG. 3). Furthermore, the compounds of formula (I) show the required conformational arrangement of the functional groups in order to fully or partially map the other points of the pharmacophore hypothesis in a low energy conformation.

The compounds of the invention have the great advantage of lacking the chiral carbon atom with respect to the known IL-8 inhibitors belonging to the family of 2-arylpropionic acids and derivatives. The process of manufacture and purification of the known 2-arylpropionic acids and derivatives requires indeed the development of complicated enantioselective conditions or the introduction of a step of optical resolution with the consequential undesired impact on the costs of the active principle.

The compounds of the invention of formula (I) and (Ia) are generally isolated in the form of their addition salts with both organic and inorganic pharmaceutically acceptable acids and bases.

Examples of such acids are selected from hydrochloric acid, sulfuric acid, phosphoric acid, metansolfonic acid, fumaric acid, citric acid.

Examples of such bases are selected from sodium hydroxide, potassium hydroxide, calcium hydroxide, (D,L)-Lysine, L-Lysine, tromethamine.

The compounds of the invention of formula I were evaluated in vitro for their ability to inhibit chemotaxis of polymorphonucleate leukocytes (hereinafter referred to as PMNs) and monocytes induced by the fractions of IL-8 and GRO-α. For this purpose, in order to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell viability was calculated by exclusion with Trypan blue, whilst the ratio of the circulating polymorphonucleates was estimated on the cytocentrifugate after staining with Diff Quick.

Human recombinant IL-8 (Pepro Tech) was used as stimulating agents in the chemotaxis experiments, giving practically identical results: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-9}$ M, for the chemotaxis assays.

During the chemotaxis assay (according to W. Falket et al., J. Immunol. Methods, 33, 239, 1980) PVP-free filters with a porosity of 5 μm and microchambers suitable for replication were used.

The compounds of the invention of formula (I) and (Ia) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula I to inhibit IL-8-induced chemotaxis of human monocytes was carried out according to the method disclosed by Van Damme J. et al. (Eur. J. Immunol., 19, 2367, 1989).

Particularly preferred is the use of compounds of formula (I) in which R groups are 3'-benzoyl, 3'-(4-chloro-benzoyl), 3'-(4-methyl-benzoyl), 3'-acetyl, 3'-propionyl, 3'-isobutanoyl, 4'-trifluoromethanesulphonyloxy, 4'-benzenesulphonyloxy, 4'-trifluoromethanesulphonylamino, 4'-benzenesulphonylamino, 4'-benzenesulphonylmethyl, 4'-acetyloxy, 4'-propionyloxy, 4'-benzoyloxy, 4' acetylamino, 4' propionylamino, 4'-benzoylamino; this activity allows the therapeutical use of these compounds in IL-8 related pathologies where the CXCR2 pathway is involved specifically or in conjunction with the CXCR1 signaling.

The dual inhibitors of the IL-8 and GRO-α induced biological activities are strongly preferred in view of the therapeutical applications of interest, but the described compounds selectively acting on CXCR1 IL-8 receptor or CXCR2 GRO-α/IL-8 receptor can find useful therapeutical applications in the management of specific pathologies as below described.

The biological activity of compounds showing high potency either as inhibitors of IL-8 induced PMN chemotaxis (CXCR1) or as dual inhibitors of IL-8 and GRO-α induced PMN chemotaxis (CXCR1/CXCR2) is reported in Table 1.

TABLE 1

Biological activity data on CXCR1 and CXCR2 receptors (% of inhibition)

| Compound | IL-8 (c = $10^{-8}$ M) | GRO-α (c = $10^{-8}$ M) |
|---|---|---|
| (5-isobutyryl-1-methyl-1H-pyrrol-2-yl)acetic acid | 58 ± 11 | 65 ± 11 |
| (5-acetyl-1-methyl-1H-pyrrol-2-yl)acetic acid | 60 ± 7 | 65 ± 5 |
| (5-acetyl-1-methyl-1H-pyrrol-2-yl)acetamide | 54 ± 10 | 44 ± 9 |
| (5-acetyl-1-methyl-1H-pyrrol-2-yl)acetyl methanesulfonamide | 50 ± 10 | 46 ± 14 |
| (4-isobutyl-2-methylphenyl)acetic acid | 60 ± 10 | 4 ± 8 |
| (3-isopropyl-2-methylphenyl)acetic acid | 62 ± 8 | 5 ± 10 |
| (4-isobutyl-2-methylphenyl)acetyl methanesulfonamide | 67 ± 14 | 0 ± 10 |
| (2-chloro-3-propionylphenyl)acetic acid | 67 ± 14 | 27 ± 8 |
| {2-methyl-4-[(trifluoromethanesulphonyl)amino]phenyl}acetyl methanesulphonamide | 60 ± 7 | 52 ± 5 |

All the compounds of the invention demonstrated a high degree of selectivity towards the inhibition of the IL-8 induced chemotaxis compared to the chemotaxis induced by C5a ($10^{-9}$ M) or f-MLP ($10^{-8}$ M).

The compounds of formula (I) and (Ia) were found to be totally ineffective as inhibitors of cyclooxygenase (COX) enzymes. In most cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15-20% of the basal value. The reduced effectiveness in the inhibition of the COX constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

In view of the experimental evidence discussed above and of the role performed by Interleukin-8 (IL-8) and congenetics thereof in the processes that involve the activation and the infiltration of neutrophils, the compounds of the invention are particularly useful in the treatment of a disease such as psoriasis (R. J. Nicholoff et al., Am. J. Pathol., 138, 129, 1991). Further diseases which can be treated with the compounds of the present invention are intestinal chronic inflammatory pathologies such as ulcerative colitis (Y. R. Mahida et al., Clin. Sci., 82, 273, 1992) and melanoma, chronic obstructive pulmonary disease (COPD), bullous pemphigoid, rheumatoid arthritis (M. Selz et al., J. Clin. Invest., 87, 463, 1981), idiopathic fibrosis (E. J. Miller, previously cited, and P. C. Cane et al., J. Clin. Invest., 88, 1882, 1991), glomerulonephritis (T. Wada et al., J. Exp. Med., 180, 1135, 1994) and in the prevention and treatment of damages caused by ischemia and reperfusion.

Inhibitors of CXCR1 and CXCR2 activation find useful applications, as above detailed, particularly in treatment of chronic inflammatory pathologies (e.g. psoriasis) in which the activation of both IL-8 receptors is supposed to play a crucial pathophysiological role in the development of the disease.

In fact, activation of CXCR1 is known to be essential in IL-8-mediated PMN chemotaxis (Hammond M et al, J Immunol, 155, 1428, 1995). On the other hand, activation of CXCR2 activation is supposed to be essential in IL-8-mediated epidermal cell proliferation and angiogenesis of psoriatic patients (Kulke R et al., J Invest Dermatol, 110, 90, 1998).

In addition, CXCR2 selective antagonists find particularly useful therapeutic applications in the management of important pulmonary diseases like chronic obstructive pulmonary disease COPD (D. W P Hay and H. M. Sarau., Current Opinion in Pharmacology 2001, 1:242-247).

It is therefore a further object of the present invention to provide the use of compounds of formula (I) and (Ia) in the preparation of a medicament for the treatment of psoriasis, ulcerative colitis, melanoma, chronic obstructive pulmonary disease (COPD), bullous pemphigoid, rheumatoid arthritis, idiopathic fibrosis, glomerulonephritis and in the prevention and treatment of damages caused by ischemia and reperfusion. The invention also provides compounds of formula (Ia) for use as medicaments.

Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the arylacetic acids of this invention and their derivatives are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acetic acid compound or its derivative usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the arylacetic acid derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

MATERIALS AND METHODS

Synthesis of Arylacetic Acids

Example 1

3-benzoyl-2-methylphenyl)acetic acid

Starting from the commercial reagent 2-hydroxy benzophenone and following the experimental procedure described in Italian Patent 1,283,649, 1-[(2'-hydroxy-3'-benzoyl)phenyl]prop-2-ene has been synthesised in good yield (>75%).

To a cooled (T=−15° C.) solution of 1-[(2'-hydroxy-3'-benzoyl)phenyl]prop-2-ene (33 mmol) in dry $CH_2Cl_2$ (70 ml) N,N-diisopropylethylamine (59.7 mmol) is added and the resulting solution is left stirring for 30' at T=−15° C. Then trifluoromethanesulfonic anhydride (40.16 mmol) is dropped into the solution and at the end of the adding the mixture is left stirring for 1 h. The mixture is quenched with 2N HCl (100 mL) and the two phases are separated and debated; the organic one is washed again with 2N HCl (100 mL), with water (2×100 mL) and with a saturated solution of NaCl (2×70 ml), dried on $Na_2SO_4$ and evaporated under reduced pressure to give 1-[(2-trifluoromethanesulfonyloxy-3-benzoyl)phenyl]prop-2-ene (31.3 mmol) as an oily crude pure enough to be used in the following step.

To a solution of 1-[(2-trifluoromethanesulfonyloxy-3-benzoyl)phenyl]prop-2-ene (30 mmol) in $CH_2Cl_2$ (90 ml) water (90 mL), acetic acid (18.2 mL) and Aliquat (1.46 mmol) are added. $KMnO_4$ (103 mmol) is added portionwise in 90'. At the end of the addings the mixture is left under stirring overnight. A 10% solution of sodium metabisulfite is added dropwise until complete bleaching of the solution. The two phases are debated and separated and the organic one is washed back with a saturated solution of NaCl (2×50 ml), dried on $Na_2SO_4$ and evaporated under reduced pressure to give an oily crude that, after flash cromatography, gives 1-[(2-trifluoromethanesulfonyloxy-3-benzoyl)phenyl]acetic acid (15 mmol) as pale yellow oil.

$^1$H-NMR ($CDCl_3$): δ 7.85 (m, 2H); 7.68 (m, 2H); 7.45 (m, 4H); 3.90 (s, 2H); 2.20 (bs, 1H, COO$\underline{H}$).

1-[(2-trifluoromethanesulfonyloxy-3-benzoyl)phenyl] acetic acid (10.3 mmol) is dissolved in methyl alcohol (30 mL) and 96% $H_2SO_4$ (0.2 mL) is added. After stirring overnight at room temperature, the solvent is evaporated under reduced pressure and the crude is diluted with $CH_2Cl_2$ (50 ml) and washed with water (3×50 mL), dried on $Na_2SO_4$ and evaporated under reduced pressure to give 1-[(2-trifluoromethanesulfonyloxy-3-benzoyl)phenyl]acetic acid methyl ester as yellow oil (9.2 mmol).

$^1$H-NMR ($CDCl_3$): δ 7.80 (m, 2H); 7.65 (m, 2H); 7.45 (m, 4H); 3.90 (s, 2H); 3.72 (s, 3H).

Starting from 1-[(2-trifluoromethanesulfonyloxy-3-benzoyl)phenyl]acetic acid methyl ester, 2-methyl derivative has been prepared by means of reacting said triflate with organostannanes according the methods described by Mitchell T. N., Synthesis, 803, 1992 and Ritter K., Synthesis, 735, 1993.

The acid has been synthesized starting from 1-[(2-trifluoromethanesulfonyloxy-3-benzoyl)phenyl]acetic acid methyl ester (7.5 mmol) which has been dissolved in dry N-methyl-2-pirrolidone (25 ml); to the mixture anhydrous LiCl (22.5 mmol), triphenylarsine (0.3 mmol) and dipalladiumtribenzylidenacetone (0.14 mmol Pd) have been added. After 5' at r.t. tetramethyltin (8.4 mmol) is added and the solution is stirred for 3 h at T=60° C. After cooling the solution to r.t., the mixture is diluted with n-hexane and a saturated solution of KF is added; after filtration and separation of the phases, the organic phase is dried over $Na_2SO_4$ and evaporated under vacuum. The purification of the residue by means of flash chromatography gives (3-benzoyl-2-methylphenyl)acetic acid methyl ester. (Ritter K., Synthesis, 735, 1993 and Mitchell T. N., Synthesis, 803, 1992).

1N NaOH (5 ml) was added to a solution of the ester in 1,4-dioxane (5 ml) and the solution is stirred at room temperature overnight. After solvent evaporation the mixture is acidified to pH=2 with 2N HCl until complete precipitation of the product, which is isolated as a white solid by filtration.

$^1$H-NMR ($CDCl_3$): δ 10.50 (bs, 1H, COO$\underline{H}$); 7.80 (m, 2H); 7.65 (m, 2H); 7.45 (m, 4H); 3.45 (s, 2H); 2.25 (s, 3H).

Example 2

(3-isopropyl-2-methylphenyl)acetic acid

According to the procedure described in Italian Patent 1,283,649 and starting from the commercial reagent T-hydroxyacetophenone, the intermediate 1-[(2-trifluoromethanesulfonyloxy-3-isopropyl)phenyl]acetic acid methyl ester has been synthesised.

$^1$H-NMR ($CDCl_3$): δ 7.55-7.40 (m, 3H); 3.85 (s, 2H); 3.70 (s, 3H); 2.45 (s, 3H).

A solution of 1-[(2-trifluoromethanesulfonyloxy-3-isopropyl)phenyl]acetic acid methyl ester (7.5 mmol) in dry THF (Tetrahydrofuran) (5 mL) is slowly dropped into a mixture of methyltriphenylphosphonium bromide (7.5 mmol) and n-BuLi (7.5 mmol; 1.6 M in n-hexane) in thy THF (10 mL). At the end of the addings the mixture is left under stirring overnight at room temperature. A 10% solution of sodium metabisulfite (20 mL) is added dropwise and the two phases are debated and separated; the organic phase is dried over $Na_2SO_4$ and evaporated under vacuum. The purification of the residue by means of flash chromatography gives 1-[(2-trifluoromethanesulfonyloxy-3-isopropen-2'-yl)phenyl]acetic acid methyl ester as colourless oil (5.28 mmol).

$^1$H-NMR ($CDCl_3$): δ 7.55-7.40 (m, 3H); 5.50 (s, 2H); 3.80 (s, 2H); 3.74 (s, 3H); 1.63 (s, 3H).

The reduction of 1-[(2-trifluoromethanesulfonyloxy-3-isopropen-2'-yl)phenyl]acetic acid methyl ester has been carried out by hydrogenolysis with Pd/C in absolute ethyl alcohol to give after catalyst filtration and mother liquors evaporation under reduced pressure, pure (3-isopropyl-2-methylphenyl)acetic acid methyl ester as pale yellow oil (5 mmol).

$^1$H-NMR ($CDCl_3$): δ 7.52-7.45 (m, 3H); 3.82 (s, 2H); 3.70 (s, 3H); 2.65 (m, 1H); 1.25 (d, 6H, J=8 Hz).

Following the procedure described for Example 1 and starting from (3-isopropyl-2-methylphenyl)acetic acid methyl ester (7.0 mmol) pure (3-isopropyl-2-methylphenyl)acetic acid has been synthesised (5.45 mmol).

$^1$H-NMR (CDCl$_3$): δ 11.2 (bs, 1H, COOH); 7.35-7.20 (m, 3H); 3.80 (s, 2H); 2.55 (m, 1H); 2.22 (s, 3H); 1.28 (d, 6H, J=8 Hz).

Example 3

(2-chloro-3-propionylphenyl)acetic acid

According to the procedure described in Italian Patent 1,283,649 and starting from the commercial reagent 2'-hydroxypropiophenone, the intermediate 1-[(2-hydroxy-3-propionyl)phenyl]prop-2-ene has been synthesised.

By treatment of the compound by PhPCl$_4$, according to the procedure described by Bay et al., J. Org. Chem., Vol. 32, 3415, 1990, 1-[(2-chloro-3-propionyl)phenyl]prop-2-ene (5.1 mmol). Following the procedure for the double bond oxidation described in the Example 1, pure (2-chloro-3-propionylphenyl)acetic acid has been synthesised (4.15 mmol).

$^1$H-NMR (CDCl$_3$): δ 10.18 (bs, 1H, COOH); 7.40-7.24 (m, 3H); 3.65 (s, 2H); 2.75 (q, 2H, J$_1$=8 Hz, J$_2$=3 Hz); 1.15 (t, 3H, J=8 Hz).

Example 4

(4-isobutyl-2-methylphenyl)acetic acid

The compound has been prepared by double Stille reaction on the starting reagent 2-(2-acetoxy-4-perfluorbutanesulfonyloxy)phenylacetic acid methyl ester (prepared according known procedures) following the same experimental procedure used for the synthesis of analogous arylpropionic acids and described in WO 01/58852 A2.

$^1$H-NMR (CDCl$_3$): δ 7.22 (d, 1H, J=8 Hz); 7.05 (d, 1H, J=8 Hz); 6.92 (s, 1H); 3.50 (s, 2H); 2.40 (d, 2H, J=7 Hz); 2.20 (s, 3H); 1.95 (m, 1H); 0.95 (d, 6H, J=7 Hz).

Example 5

{2-methyl-4-[(phenylsulphonyl)amino]phenyl}acetic acid

The synthesis of the compound has been carried out as follows:
the commercial reagent 2-hydroxy-4-nitrobenzoic acid has been transformed into 2-hydroxy-4-nitroacetophenone by the Meldrum's acid pathway to methyl ketones, according to the experimental procedure described by Hase T. A. et al., Synthetic Communications, 10(3), 221-224, 1980. The treatment of 2-hydroxy-4-nitroacetophenone with trifluoromethanesulfonic anhydride has given the 2-trifluoromethanesulfonyloxy derivative that, by Stile reaction according the experimental procedure described in Example 1, has afforded the 2-methyl-4-nitroacetophenone.

Starting from 2-methyl-4-nitroacetophenone and following the procedure described in Italian Patent 1,283,649 the 2-methyl-4-nitro phenylacetic acid methyl ester has been synthesised.

$^1$H-NMR (CDCl$_3$): δ 7.50-7.42 (m, 3H); 3.80 (s, 2H); 3.64 (s, 3H); 2.25 (s, 3H).

To a solution of 2-methyl-4-nitro phenylacetic acid methyl ester (10 mmol) in dry THF (20 mL) and methyl alcohol (20 mL), ammonium formate (0.1 mol) and 10% Pd/C (0.5 g) have been added and the resulting mixture has been left stirring for 3 h, until complete disappearance of the starting reagent. The catalyst has been filtered off and the filtrate evaporated under vacuum to give 2-methyl-4-amino phenylacetic acid methyl ester as a waxy solid (9.22 mmol).

$^1$H-NMR (CDCl$_3$): δ 7.51 (m, 1H); 7.40 (m, 1H); 7.15 (m, 1H); 5.00 (bs, 2H, NH$_2$); 3.82 (s, 2H); 3.65 (s, 3H); 2.20 (s, 3H).

To a solution of 2-methyl-4-amino phenylacetic acid methyl ester (5.3 mmol) in acetone (10 mL) dry pyridine (7.95 mmol) and phenylsulfonyl chloride (6.36 mmol) have been added and the resulting solution has been left stirring overnight at room temperature. Acetone has been evaporated and the residue diluted with CHCl$_3$ (15 mL), washed with 1N HCl (2×10 mL), water (3×20 mL), dried over Na$_2$SO$_4$ and evaporated under vacuum to give {2-methyl-4-[(phenylsulphonyl)amino]phenyl}acetic acid methyl ester as colourless oil (5.0 mmol) pure to be used in the following reaction. Following the procedure described for Example 1 and starting from the methyl ester (5.0 mmol) pure {2-methyl-4-[(phenylsulphonyl)amino]phenyl}acetic acid has been synthesised (4.75 mmol).

$^1$H-NMR (CDCl$_3$): δ 9.40 (s, 1H, SO$_2$NH); 7.73 (m, 2H); 7.42 (m, 3H); 7.50 (m, 1H); 7.45 (m, 1H); 7.15 (m, 1H); 3.82 (s, 2H); 2.21 (s, 3H).

According to the same experimental procedure and using as reagent trifluoromethanesulfonic anhydride, the following compound has been synthesised:

Example 6

{2-methyl-4-[(trifluoromethanesulfonyl)amino]phenyl}acetic acid $^1$H-NMR (CDCl$_3$): δ 9.35 (s, 1H, SO$_2$NH); 7.54 (m, 1H); 7.40 (m, 1H); 7.20 (m, 1H); 3.80 (s, 2H); 2.25 (s, 3H).

Example 7

{2-chloro-4-[(trifluoromethanesulfonyl)oxy]phenyl}acetic acid

Starting from the intermediate 2-hydroxy-4-nitroacetophenone (described in the Example 5), the synthesis of the 2-chloro derivative has been carried out following the experimental procedure described by Bay et al., J. Org. Chem., Vol. 32, 3415, 1990. The intermediate 2-chloro-4-nitroacetophenone has been transformed into the intermediate 2-chloro-4-amino phenylacetic acid methyl ester according the same procedure described in Example 5.

$^1$H-NMR (CDCl$_3$): δ 7.55-7.45 (m, 3H); 3.85 (s, 2H); 3.60 (s, 3H).

After treatment of 2-chloro-4-amino phenylacetic acid methyl ester with sodium nitrite in acidic conditions and following replacement of the diazonium ion with the hydroxyl group as described in Organic Synthesis, III, 453, (2-chloro-4-hydroxyphenyl)acetic acid has been obtained as white solid.

$^1$H-NMR (CDCl$_3$): δ 7.74-7.60 (m, 3H); 6.35 (bs, 1H, OH); 3.85 (s, 2H).

A mixture of the above described (2-chloro-4-hydroxyphenyl)acetic acid (2 mmol), trifluoromethanesulfonic anhydride (4 mmol) in dry pyridine (1 mL) has been warmed at T=60° C. for 24 hours. After cooling at room temperature the reaction mixture has been poured into 1 N HCl (5 mL) and the aqueous solution extracted with CH$_2$Cl$_2$ (3×10 mL). The collected organic extracts have been washed back with 1N NaOH (2×10 mL), dried over Na$_2$SO$_4$ and evaporated under reduced pressure to give a crude residue. The crystallisation in isopropyl ether of the crude has given the pure {2-chloro-4-[(trifluoromethanesulfonyl)oxy]phenyl}acetic acid as white solid (1.25 mmol).

$^1$H-NMR (CDCl$_3$): δ 7.70-7.62 (m, 3H); 3.85 (s, 2H).

Example 8

(5-benzoyl-1-methyl-1H-pyrrol-2-yl)acetic acid

The compound has been synthesised starting from the commercial reagents 1-methyl-2-pyrrolecarboxaldehyde and benzoyl chloride and following the experimental procedure described in Di Santo R. et al. Synth. Comm., 25(6), 787-793 (1995).

$^1$H-NMR (CDCl$_3$): δ 7.85 (m, 2H); 7.52 (m, 1H); 7.45 (m, 2H); 6.70 (s, 1H); 6.15 (s, 1H); 3.97 (s, 3H); 3.75 (s, 2H); 3.0 (bs, 1H, COO$\underline{H}$).

According the same experimental procedures and starting from the related commercial acyl chlorides, the following compounds have been prepared:

Example 9

[1-methyl-5-(4-chlorobenzoyl)-1H-pyrrol-2-yl]acetic acid $^1$H-NMR (CDCl$_3$): δ 7.82 (d, 2H, J=8 Hz); 7.58 (d, 2H, J=8 Hz); 7.20 (s, 1H); 6.68 (s, 1H); 3.75 (s, 2H); 3.70 (s, 3H).

Example 10

[1-methyl-5-[(4-methylbenzoyl)-1H-pyrrol-2-yl]acetic acid $^1$H-NMR (CDCl$_3$): δ 7.80 (d, 2H, J=8 Hz); 7.55 (d, 2H, J=8 Hz); 7.18 (s, 1H); 6.72 (s, 1H); 3.75 (s, 2H); 3.70 (s, 3H); 2.35 (s, 3H).

Example 11

(5-acetyl-1-methyl-1H-pyrrol-2-yl)acetic acid $^1$H-NMR (CDCl$_3$): δ 6.90 (d, 1H, J=3 Hz); 6.05 (d, 1H, J=3 Hz); 3.80 (s, 3H); 3.62 (s, 2H); 2.32 (s, 3H).

Example 12

(5-isobutyryl-1-methyl-1H-pyrrol-2-yl)acetic acid $^1$H-NMR (CDCl$_3$): δ 7.55 (s, 1H); 6.32 (s, 1H); 3.65 (s, 2H); 3.52 (s, 3H); 3.15 (m, 1H); 1.05 (d, 6H, J=7 Hz).

Example 13

(1-benzoyl-2-methyl-1H-pyrrol-3-yl)acetic acid

The intermediate (2-methyl-1H-pyrrol-3-yl)acetic acid ethyl ester has been synthesised as described in Bertschy H., et al., Angew. Chem. Int. Ed. Engl. 29(7), 777-778 (1990).

The following N-benzoylation and ester hydrolysis according well known procedures (NaH/benzoyl chloride) give the desired product.

$^1$H-NMR (CDCl$_3$): δ 8.15 (m, 2H); 7.60 (m, 1H); 7.45 (m, 2H); 6.95 (d, 1H, J=3 Hz); 6.32 (d, 1H, J=3 Hz); 4.50 (bs, 1H, COO$\underline{H}$); 3.85 (s, 2H); 2.35 (s, 3H).

Example 14

(1-benzoyl-2-chloro-1H-pyrrol-3-yl)acetic acid

The product has been synthesised by a multistep synthesis according well known literature procedures. The condensation of the commercial reagent diethyl malonate with bromoacetaldehyde dimethyl acetal and the acetal hydrolysis allows to obtain the intermediate aldehyde which, after treatment with gaseous ammonia and dehydration of the not isolated intermediate enamine, gives the pure intermediate 2-hydroxypyrrole-3-acetic acid ethyl ester.

$^1$H-NMR (CDCl$_3$): δ 10.35 (bs, 1H, N$\underline{H}$); 7.21 (d, 1H, J=3 Hz); 7.05 (bs, 1H, O$\underline{H}$); 6.35 (d, 1H, J=3 Hz); 4.12 (q, 2H, J=7 Hz); 3.45 (s, 2H); 1.31 (t, 3H, J=7 Hz).

The pyrrole intermediate, after treatment with PCl$_5$, gives the 2-chloro derivative which, after ester hydrolysis in usual conditions (NaOH/CH$_3$OH) and N-benzoylation, affords the pure compound (1-benzoyl-2-chloro-1H-pyrrol-3-yl)acetic acid as white solid (yield 78%).

$^1$H-NMR (DMSO-d$_6$): δ 8.15 (m, 2H); 7.60 (m, 1H); 7.45 (m, 2H); 6.92 (d, 1H, J=3 Hz); 6.35 (d, 1H, J=3 Hz); 4.65 (bs, 1H, COO$\underline{H}$); 3.82 (s, 2H).

Example 15

(1-benzoyl-2-methyl-1H-indol-3-yl)acetic acid

The commercial reagent 2-methyl-3-indoleacetic acid (3 mmol) has been treated with NaH (6.6 mmol) and benzoyl chloride (6.6 mmol) in dry THF (10 mL) according well known procedures. The usual reaction work up and crystallisation of the residue in isopropyl ether led to the pure (1-benzoyl-2-methyl-1H-indole-3-yl)acetic acid as white solid (2.25 mmol).

$^1$H-NMR (CDCl$_3$): δ 7.82-7.70 (m, 3H); 7.55 (t, 2H, J=8.5 Hz); 6.90-6.80 (m, 2H); 6.65 (m, 2H); 3.62 (s, 2H); 3.30 (s, 3H).

Example 16

[1-(4-chlorobenzoyl)-2-methyl-1H-indol-3-yl]acetic acid

The commercial reagent 2-methyl-3-indoleacetic acid (3 mmol) has been treated with NaH (6.6 mmol) and 4-chlorobenzoyl chloride (6.6 mmol) in dry THF (10 mL) according well known procedures. The usual reaction work up and crystallisation of the residue in isopropyl ether led to the pure [1-(4-chlorobenzoyl)-2-methyl-1H-indol-3-yl]acetic acid as white solid (2.01 mmol).

$^1$H-NMR (CDCl$_3$): δ 7.80-7.70 (t, 2H, J=8.5 Hz); 7.55 (t, 2H, J=8.5 Hz); 6.90 (s, 1H); 6.80 (m, 1H); 3.60 (s, 2H); 3.30 (s, 3H).

Example 17

(1-isopropyl-2-methyl-1H-pyrrole[2,3-b]pyridin-3-yl)acetic acid

The commercial reagent 1H-pyrrole[2,3-b]pyridine (3 mmol) has been treated with NaH (3.3 mmol) and isopropyl chloride (3.3 mmol) in dry THF (10 mL) according well known procedures. The usual reaction work up and purification of the residue by chromatography led to the pure 1-isopropyl-1H-pyrrole[2,3-b]pyridine as white solid (2.83 mmol).

$^1$H-NMR (CDCl$_3$): δ 7.65 (m, 1H); 7.15-7.08 (m, 2H); 7.00 (m, 1H); 6.50 (m, 1H); 3.12 (m, 1H); 1.05 (d, 6H, J=7 Hz).

Following the experimental procedure described by Chi S. M. et al., Tetrahedron Letters, 41, 919-922 (2000) and starting from 1-isopropyl-1H-pyrrole[2,3-b]pyridine (2.5 mmol), (1-isopropyl-2-methyl-1H-pyrrole[2,3-b]pyridin-3-yl) ethoxy acetate has been isolated (2.0 mmol). The final oxidation by KMnO$_4$ in phase transfer catalysis conditions (described in Example 1) has led to the desired product (1-isopropyl-2-methyl-1H-pyrrole[2,3-b]pyridin-3-yl)acetic acid (1.85 mmol).

$^1$H-NMR (CDCl$_3$): δ 7.15 (m, 1H); 7.10 (m, 1H); 6.95 (m, 1H); 3.55 (s, 2H); 3.11 (m, 1H); 2.35 (s, 3H); 1.05 (d, 6H, J=7 Hz).

Example 18

(3-benzoyl-2-methoxyphenyl)acetic acid (3-benzoyl-2-hydroxyphenyl)acetic acid methyl ester, prepared according know procedures from 2-hydroxybenzophenone, has been treated with potassium carbonate and iodomethane in acetone to give the corresponding 2-methoxy derivative that, after usual hydrolysis (NaOH/CH$_3$OH) has given (3-benzoyl-2-methoxyphenyl)acetic acid as white solid.

$^1$H-NMR (CDCl$_3$): δ 7.90 (d, 2H, J=7 Hz); 7.62 (m, 1H); 7.50-7.40 (m, 3H); 7.35 (m, 1H); 7.15 (t, 1H, J=7 Hz); 3.82 (s, 2H); 3.60 (s, 3H).

Synthesis of Arylacetic Amides

According to the experimental procedure described in WO 01/58852 and starting from the related acetic acid, the following compounds have been synthesised:

Example 19

(5-acetyl-1-methyl-1H-pyrrol-2-yl)acetamide $^1$H-NMR (CDCl$_3$): δ 6.92 (d, 1H, J=3 Hz); 6.05 (d, 1H, J=3 Hz); 5.25 (bs, 2H, CONH$_2$); 3.81 (s, 3H); 3.68 (s, 2H); 2.35 (s, 3H).

Example 20

(5-acetyl-1-methyl-1H-pyrrol-2-yl)-N-carboxymethylacetamide $^1$H-NMR (CDCl$_3$): δ 6.90 (d, 1H, J=3 Hz); 6.05 (d, 1H, J=3 Hz); 5.95 (d, 1H, J=7 Hz, CONH); 4.05 (d, 2H, J=7 Hz); 3.81 (s, 3H); 3.68 (s, 2H); 2.35 (s, 3H).

Example 21

(S)(5-acetyl-1-methyl-1H-pyrrol-2-yl)-N-(2-carboxyethyl)acetamide $^1$H-NMR (CDCl$_3$): δ 6.92 (d, 1H, J=3 Hz); 6.05 (d, 1H, J=3 Hz); 6.00 (bs, 1H, CONH); 4.53 (q, 1H, J=7 Hz); 3.81 (s, 3H); 3.68 (s, 2H); 2.35 (s, 3H); 1.55 (d, 3H, J=7 Hz).

Example 22

(5-acetyl-1-methyl-1H-pyrrol-2-yl)-N-(3-dimethylaminopropyl)acetamide $^1$H-NMR (CDCl$_3$): δ 7.75 (bs, 1H, CONH); 6.92 (d, 1H, J=3 Hz); 6.28 (d, 1H, J=3 Hz); 4.10 (s, 3H); 3.80 (s, 2H); 3.54 (m, 2H); 2.48 (t, 2H, J=7 Hz); 2.40 (s, 3H); 2.19 (s, 6H); 1.76 (m, 2H).

Example 23

(S)(5-acetyl-1-methyl-1H-pyrrol-2-yl)-N-(1-carboxy-2-methoxyethyl)acetamide $^1$H-NMR (CDCl$_3$): δ 7.45 (bs, 1H, CONH); 6.92 (d, 1H, J=3 Hz); 6.05 (d, 1H, J=3 Hz); 4.53 (q, 1H, J=7 Hz); 3.81 (s, 3H); 3.68 (s, 2H); 3.20 (s, 3H); 3.15 (d, 2H, J=7 Hz); 2.35 (s, 3H).

Example 24

(4-isobutyl-2-methylphenyl)acetamide $^1$H-NMR (CDCl$_3$): δ 7.20 (d, 1H, J=8 Hz); 7.05 (d, 1H, J=8 Hz); 6.95 (s, 1H); 5.70 (bs, 2H, CONH$_2$); 3.68 (s, 2H); 2.40 (d, 2H, J=7 Hz); 2.22 (s, 3H); 1.95 (m, 1H); 0.95 (d, 6H, J=7 Hz).

Example 25

(2-chloro-3-propionylphenyl)-N-(3-dimethylaminoethyl)acetamide $^1$H-NMR (CDCl$_3$): δ 7.50 (bs, 1H, CONH); 7.40-7.24 (m, 3H); 3.62 (s, 2H); 3.54 (m, 2H); 2.75 (q, 2H, J$_1$=8 Hz, J$_2$=3 Hz); 2.25 (t, 2H, J=7 Hz); 2.19 (s, 6H); 1.15 (t, 3H, J=8 Hz).

Example 26

(3-isopropyl-2-methylphenyl)-N-[3-(1-piperidinyl)propyl]acetamide $^1$H-NMR (CDCl$_3$): δ 7.45 (bs, 1H, CONH); 7.35-7.20 (m, 3H); 3.80 (s, 2H); 3.50 (m, 2H); 3.32 (m, 2H); 2.95 (m, 2H); 2.55 (m, 1H); 2.45 (m, 2H); 2.22 (s, 3H); 2.10 (m, 2H); 1.90 (m, 6H); 1.28 (d, 6H, J=8 Hz).

Example 27

(3-benzoyl-2-methylphenyl)acetamide $^1$H-NMR (CDCl$_3$): δ 7.82 (m, 2H); 7.60 (m, 2H); 7.45 (m, 4H); 5.45 (bs, 2H, CONH$_2$); 3.70 (s, 2H); 2.25 (s, 3H).

Example 28

(1-benzoyl-2-methyl-1H-indol-3-yl)acetamide $^1$H-NMR (CDCl$_3$): δ 7.82-7.70 (m, 3H); 7.55 (t, 2H, J=8.5 Hz); 6.90-6.80 (m, 2H); 6.65 (m, 2H); 5.75 (bs, 2H, CONH$_2$); 3.68 (s, 2H); 3.30 (s, 3H).

Example 29

(1-benzoyl-2-methyl-1H-indol-3-yl)-N-(3-dimethylaminopropyl)acetamide $^1$H-NMR (CDCl$_3$): δ 7.80-7.72 (m, 3H); 7.60 (bs, 1H, CONH); 7.55 (t, 2H, J=8.5 Hz); 6.90-6.80 (d, 2H, J=8 Hz);

6.65 (d, 2H, J=8 Hz); 3.80 (s, 2H); 3.58 (m, 2H); 3.30 (s, 3H); 2.50 (t, 2H, J=7 Hz); 2.20 (s, 6H); 1.80 (m, 2H).

Example 30

[1-(4-chlorobenzoyl)-2-methyl-1H-indol-3-yl]acetamide $^1$H-NMR (CDCl$_3$): δ 7.80-7.70 (m, 2H, J=8.5 Hz); 7.55 (t, 2H, J=8.5 Hz); 6.92-6.80 (d, 2H, J=8 Hz); 6.68 (d, 2H, J=8 Hz); 5.62 (bs, 2H, CONH$_2$); 3.70 (s, 2H); 3.30 (s, 3H).

Example 31

[1-(4-chlorobenzoyl)-5-methoxy-2-methyl-1H-indol-3-yl]acetamide $^1$H-NMR (CDCl$_3$): δ 7.82-7.75 (m, 2H, J=8.5 Hz); 7.55 (m, 2H); 6.92-6.70 (m, 3H); 5.60 (bs, 2H, CONH$_2$); 3.82 (s, 3H); 3.66 (s, 2H); 3.30 (s, 3H).

Example 32

{2-chloro-4-[(trifluoromethanesulfonyl)oxy]phenyl}-N-(2-hydroxyethoxyethyl)acetamide $^1$H-NMR (CDCl$_3$): δ 7.70-7.62 (m, 3H); 5.90 (bs, 1H, CONH); 3.80 (s, 2H); 3.65 (m, 2H); 3.55-3.32 (m, 6H); 2.05 (bs, 1H, OH).

Example 33

(1-benzoyl-2-methyl-1H-pyrrol-3-yl)-N-(2-methoxyethyl)acetamide $^1$H-NMR (CDCl$_3$): δ 8.12 (m, 2H); 7.60 (m, 1H); 7.50 (m, 2H); 6.92 (d, 1H, J=3 Hz); 6.32 (d, 1H, J=3 Hz); 5.65 (bs, 1H, CONH); 3.75 (s, 2H); 3.25 (t, 2H, J=8 Hz); 3.20 (s, 3H); 2.97 (m, 2H); 2.35 (s, 3H).

Example 34

(1-benzoyl-2-chloro-1H-pyrrol-3-yl)-N-[3-(1-morpholino)propyl]acetamide $^1$H-NMR (CDCl$_3$): δ 8.15 (m, 2H); 7.60 (m, 1H); 7.45 (m, 2H); 6.92 (d, 1H, J=3 Hz); 6.35 (d, 1H, J=3 Hz); 6.20 (bs, 1H, CONH); 3.78 (s, 2H); 3.25 (m, 4H); 2.98 (m, 2H); 2.45 (m, 6H); 1.80 (m, 2H).

Example 35

(5-isobutyryl-1-methyl-1H-pyrrol-2-yl)acetamide $^1$H-NMR (CDCl$_3$): δ 7.50 (s, 1H); 6.35 (s, 1H); 5.85 (bs, 2H, CONH$_2$); 3.77 (s, 2H); 3.50 (s, 3H); 3.18 (m, 1H); 1.05 (d, 6H, J=7 Hz).

Example 36

(5-benzoyl-1-methyl-1H-pyrrol-2-yl)-N-(2-carboxymethyl)acetamide $^1$H-NMR (CDCl$_3$): δ 10.53 (bs, 1H, COOH), 7.85 (m, 2H); 7.52 (m, 1H); 7.45 (m, 2H); 6.70 (s, 1H); 6.15 (s, 1H); 5.95 (d, 1H, J=7 Hz, CONH); 4.05 (d, 2H, J=7 Hz) 3.95 (s, 3H); 3.68 (s, 2H).

Example 37

[1-methyl-5-(4-chlorobenzoyl)-1H-pyrrol-2-yl]-N-(2-hydroxyethoxyethyl)acetamide $^1$H-NMR (CDCl$_3$): δ 7.82 (d, 2H, J=8 Hz); 7.55 (d, 2H, J=8 Hz); 7.40 (bs, 1H, CONH); 7.35 (s, 1H); 6.65 (s, 1H); 3.70 (s, 2H); 3.65 (s, 3H); 3.60 (m, 2H); 3.50-3.42 (m, 6H); 2.25 (bs, 1H, OH).

Example 38

[1-methyl-5-(4-chlorobenzoyl)-1H-pyrrol-2-yl]acetamide $^1$H-NMR (CDCl$_3$): δ 7.82 (d, 2H, J=8 Hz); 7.58 (d, 2H, J=8 Hz); 7.20 (s, 1H); 6.68 (s, 1H); 6.35 (bs, 2H, CONH$_2$); 3.70 (s, 3H); 3.66 (s, 2H).

Example 39

{2-methyl-4-[(phenylsulphonyl)amino]phenyl}-N-(3-dimethylaminopropyl)acetamide $^1$H-NMR (CDCl$_3$); δ 9.20 (s, 1H, SO$_2$NH); 7.75 (m, 2H); 7.65 (bs, 1H, CONH); 7.42 (m, 3H); 7.50 (m, 1H); 7.45 (m, 1H); 7.12 (m, 1H); 3.88 (s, 2H); 3.58 (m, 2H); 2.50 (t, 2H, J=7 Hz); 2.35 (s, 6H); 2.21 (s, 3H); 1.80 (m, 2H).

Example 40

(3-benzoyl-2-methoxyphenyl)acetamide $^1$H-NMR (CDCl$_3$): δ 7.90 (d, 2H, J=7 Hz); 7.62 (m, 1H); 7.50-7.40 (m, 3H); 7.35 (m, 1H); 7.15 (t, 1H, J=7 Hz); 6.55 (bs, 2H, CONH$_2$); 3.82 (s, 3H); 3.66 (s, 2H).

Synthesis of Arylacetic Methanesulfonamides

According to the experimental procedure described in WO 00/24710 and starting from the related acetic acid, the following compounds have been synthesised:

Example 41

(5-acetyl-1-methyl-1H-pyrrol-2-yl)acetyl methanesulfonamide $^1$H-NMR (CDCl$_3$): δ 7.50 (bs, 1H, CONH); 6.90 (d, 1H, J=3 Hz); 6.05 (d, 1H, J=3 Hz); 3.80 (s, 3H); 3.58 (s, 2H); 3.22 (s, 3H); 2.32 (s, 3H).

Example 42

(4-isobutyl-2-methylphenyl)acetyl methanesulfonamide $^1$H-NMR (CDCl$_3$): δ 7.20 (d, 1H, J=8 Hz); 7.10 (bs, 1H, CONH); 7.00 (d, 1H, J=8 Hz); 6.85 (s, 1H); 3.65 (s, 2H); 3.22 (s, 3H); 2.40 (d, 2H, J=7 Hz); 2.22 (s, 3H); 1.95 (m, 1H); 0.95 (d, 6H, J=7 Hz).

Example 43

{2-methyl-4-[(trifluoromethanesulfonyl)amino]phenyl}acetyl methanesulfonamide $^1$H-NMR (CDCl$_3$): δ 9.42 (bs, 1H, SO$_2$N<u>H</u>); 7.45 (bs, 1H, CON<u>H</u>); 7.52 (m, 1H); 7.45 (m, 1H); 7.20 (m, 1H); 3.85 (s, 2H); 3.45 (s, 3H); 2.25 (s, 3H).

Example 44

[1-methyl-5-[(4-methylbenzoyl)-1H-pyrrol-2-yl]acetyl methanesulfonamide $^1$H-NMR (CDCl$_3$); δ 7.80 (d, 2H, J=8 Hz); 7.55 (d, 2H, J=8 Hz); 7.38 (bs, 1H, CON<u>H</u>); 7.18 (s, 1H); 6.72 (s, 1H); 3.82 (s, 2H); 3.70 (s, 3H); 3.42 (s, 3H); 2.35 (s, 3H).

Table II reports chemical name and structure formula for the compounds of Examples 1-44.

TABLE (II)

| N. | Compound name | Structure formula |
|---|---|---|
| 1 | (3-benzoyl-2-methylphenyl)acetic acid | |
| 2 | (3-isopropyl-2-methylphenyl)acetic acid | |
| 3 | (2-chloro-3-propionylphenyl)acetic acid | |
| 4 | (4-isobutyl-2-methylphenyl)acetic acid | |
| 5 | {2-methyl-4-[(phenylsulfonyl)amino]phenyl}acetic acid | |
| 6 | (2-methyl-4-{[(trifluoromethyl)sulfonyl]amino}phenyl)acetic acid | |
| 7 | (2-chloro-4-{[(trifluoromethyl)sulfonyl]oxy}phenyl)acetic acid | |

TABLE (II)-continued

| N. | Compound name | Structure formula |
|---|---|---|
| 8 | (5-benzoyl-1-methyl-1H-pyrrol-2-yl)acetic acid | |
| 9 | [5-(4-chlorobenzoyl)-1-methyl-1H-pyrrol-2-yl]acetic acid | |
| 10 | [1-methyl-5-(4-methylbenzoyl)-1H-pyrrol-2-yl]acetic acid | |
| 11 | (5-acetyl-1-methyl-1H-pyrrol-2-yl)acetic acid | |
| 12 | (5-isobutyryl-1-methyl-1H-pyrrol-2-yl)acetic acid | |
| 13 | (1-benzoyl-2-methyl-1H-pyrrol-3-yl)acetic acid | |
| 14 | (1-benzoyl-2-chloro-1H-pyrrol-3-yl)acetic acid | |

TABLE (II)-continued

| N. | Compound name | Structure formula |
|---|---|---|
| 15 | (1-benzoyl-2-methyl-1H-indol-3-yl)acetic acid | |
| 16 | [1-(4-chlorobenzoyl)-2-methyl-1H-indol-3-yl]acetic acid | |
| 17 | (1-isopropyl-2-methyl-1H-pyrrolo[2,3-b]pyridin-3-yl)acetic acid | |
| 18 | (3-benzoyl-2-methoxyphenyl)acetic acid | |
| 19 | (5-acetyl-1-methyl-1H-pyrrol-2-yl)acetamide | |
| 20 | (5-acetyl-1-methyl-1H-pyrrol-2-yl)-N-carboxymethylacetamide | |
| 21 | (S)(5-acetyl-1-methyl-1H-pyrrol-2-yl)-N-(2-carboxyethyl)acetamide | |

TABLE (II)-continued

| N. | Compound name | Structure formula |
|---|---|---|
| 22 | (5-acetyl-1-methyl-1H-pyrrol-2-yl)-N-(3-dimethylaminopropyl)acetamide | |
| 23 | (S)(5-acetyl-1-methyl-1H-pyrrol-2-yl)-N-(1-carboxy-2-methoxyethyl)acetamide | |
| 24 | (4-isobutyl-2-methylphenyl)acetamide | |
| 25 | (2-chloro-3-propionylphenyl)-N-(3-dimethylaminoethyl)acetamide | |
| 26 | (3-isopropyl-2-methylphenyl)-N-[3-(1-piperidinyl)propyl]acetamide | |
| 27 | (3-benzoyl-2-methylphenyl)acetamide | |
| 28 | (1-benzoyl-2-methyl-1H-indol-3-yl)acetamide | |

TABLE (II)-continued

| N. | Compound name | Structure formula |
|---|---|---|
| 29 | (1-benzoyl-2-methyl-1H-indol-3-yl)-N-(3-dimethylaminopropyl)acetamide | |
| 30 | [1-(4-chlorobenzoyl)-2-methyl-1H-indol-3-yl]acetamide | |
| 31 | [1-(4-chlorobenzoyl)-5-methoxy-2-methyl-1H-indol-3-yl]acetamide | |
| 32 | {2-chloro-4-[(trifluoromethanesulfonyl)oxy]phenyl}-N-(2-hydroxyethoxyethyl)acetamide | |
| 33 | (1-benzoyl-2-methyl-1H-pyrrol-3-yl)-N-(2-methoxyethyl)acetamide | |

TABLE (II)-continued

| N. | Compound name | Structure formula |
|---|---|---|
| 34 | (1-benzoyl-2-chloro-1H-pyrrol-3-yl)-N-[3-(1-morpholino)propyl]acetamide | 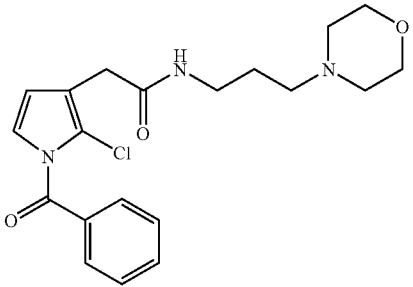 [SMILES: O=C(Cc1ccn(C(=O)c2ccccc2)c1Cl)NCCCN1CCOCC1] |
| 35 | (5-isobutyryl-1-methyl-1H-pyrrol-2-yl)acetamide | 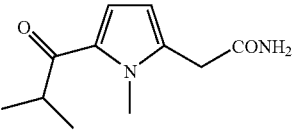 |
| 36 | (5-benzoyl-1-methyl-1H-pyrrol-2-yl)-N-(2-carboxymethyl)acetamide | 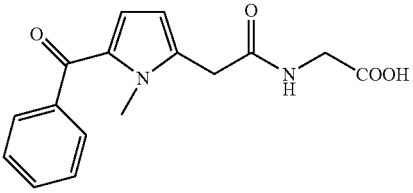 [SMILES: Cn1c(CC(=O)NCC(=O)O)ccc1C(=O)c1ccccc1] |
| 37 | [1-methyl-5-(4-chlorobenzoyl)1H-pyrrol-2-yl]-N-(2-hydroxyethoxyethyl)acetamide | 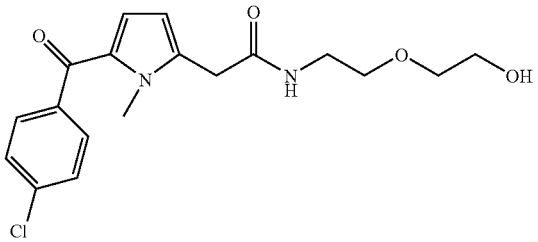 [SMILES: Cn1c(CC(=O)NCCOCCO)ccc1C(=O)c1ccc(Cl)cc1] |
| 38 | [1-methyl-5-(4-chlorobenzoyl)1H-pyrrol-2-yl]acetamide | 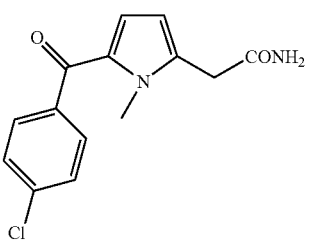 [SMILES: Cn1c(CC(N)=O)ccc1C(=O)c1ccc(Cl)cc1] |
| 39 | {2-methyl-4-[(phenylsulfonyl)amino]phenyl}-N-(3-dimethylaminopropyl)acetamide | 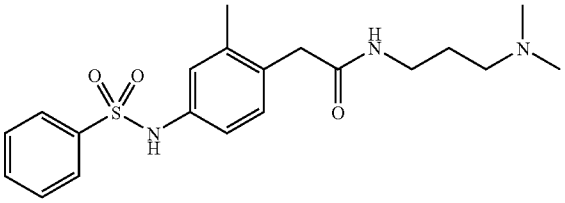 [SMILES: Cc1cc(NS(=O)(=O)c2ccccc2)ccc1CC(=O)NCCCN(C)C] |
| 40 | (3-benzoyl-2-methoxyphenyl)acetamide | 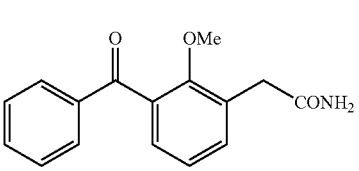 [SMILES: COc1c(CC(N)=O)cccc1C(=O)c1ccccc1] |

TABLE (II)-continued

| N. | Compound name | Structure formula |
|---|---|---|
| 41 | (5-acetyl-1-methyl-1H-pyrrol-2-yl)acetyl methanesulfonamide | |
| 42 | (4-isobutyl-2-methylphenyl)acetyl methanesulfonamide | |
| 43 | {2-methyl-4-[trifluoromethanesulfonyl)amino]phenyl}acetyl methanesulfonamide | |
| 44 | [1-methyl-5-(4-methylbenzoyl)-1H-pyrrol-2-yl]acetyl methanesulfonamide | |

The invention claimed is:

1. A method of treatment of psoriasis, ulcerative colitis, chronic obstructive pulmonary disease (COPD), bullous pemphigoid, idiopathic fibrosis, glomerulonephritis and in the prevention and treatment of ischemia-reperfusion injury comprising administering a compound of formula (I):

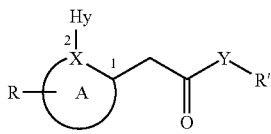

or a pharmaceutically acceptable salt thereof,
wherein
A is selected from the group consisting of benzene, pyrrole, and indole;
labels 1 and 2 mark the relevant positions on the A ring;
the X atom is nitrogen or carbon;
R is a substituting group on the A ring selected from the group consisting of:
  a group in the 3 (meta) position that is linear or branched $C_1$-$C_5$-alkyl, linear or branched $C_2$-$C_5$-alkenyl, linear or branched $C_2$-$C_5$-alkynyl, or substituted or not-substituted phenyl, linear or branched $C_1$-$C_5$-hydroxyalkyl, $C_2$-$C_5$-acyl, substituted or not-substituted benzoyl; and
  a group in the 4 (para) position that is $C_1$-$C_5$ alkyl, $C_2$-$C_5$-alkenyl, $C_2$-$C_5$-alkynyl, $C_3$-$C_6$-cycloalkyl, $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, 2-furyl; 3-tetrahydrofuryl; 2-thiophenyl; 2-tetrahydrothiophenyl, $C_1$-$C_8$-alkanoyl, cycloalkanoyl or arylalkanoyl-$C_1$-$C_5$-alkylamino;
Hy is selected from the group consisting of methyl, ethyl, chlorine, bromine, methoxy and trifluoromethyl; and
YR' is OH.

2. The method according to claim 1, wherein R is 3'-benzoyl, 3'-(4-chloro-benzoyl), 3'-(4-methyl-benzoyl), 3'-acetyl, 3'-propionyl, 3'-isobutanoyl, 3'-ethyl, 3'-isopropyl, 4'-isobutyl, 4'-trifluoromethanesulphonyloxy, 4'-benzenesulphonyloxy, 4'-trifluoromethanesulphonylamino, 4'-benzenesulphonylamino, 4'-benzenesulphonylmethyl, 4'-acetyloxy, 4'-propionyloxy, 4'-benzoyloxy, 4'-acetylamino, 4'-propionylamino, or 4'-benzoylamino.

3. A method of treatment of psoriasis, ulcerative colitis, chronic obstructive pulmonary disease (COPD), bullous pemphigoid, idiopathic fibrosis, glomerulonephritis and in the prevention and treatment of ischemia-reperfusion injury comprising administering a compound that is selected from the group consisting of:
  (3-benzoyl-2-methylphenyl)acetic acid,
  (2-chloro-3-propionylphenyl)acetic acid,
  (3-isopropyl-2-methylphenyl)acetic acid,
  (4-isobutyl-2-methylphenyl)acetic acid,
  {2-methyl-4-[(phenylsulphonyl)amino]phenyl}acetic acid,
  {2-methyl-4-[(trifluoromethanesulphonyl)amino]phenyl}acetic acid,
  {2-chloro-4-[(trifluoromethanesulphonyl)oxy]phenyl}acetic acid,
  (5-acetyl-1-methyl-1H-pyrrol-2-yl)acetic acid,

[1-methyl-5-(4-methylbenzoyl)-1H-pyrrol-2-yl]acetic acid,
(5-benzoyl-1-methyl-1H-pyrrol-2-yl)acetic acid,
[1-methyl-5-(4-chlorobenzoyl)-1H-pyrrol-2-yl]acetic acid,
(5-isobutyryl-1-methyl-1H-pyrrol-2-yl)acetic acid,
(1-benzoyl-2-methyl-1H-pyrrol-3-yl)acetic acid,
(1-benzoyl-2-chloro-1H-pyrrol-3-yl)acetic acid,
(1-benzoyl-2-methyl-1H-indol-3-yl)acetic acid,
[1-(4-chlorobenzoyl)-2-methyl-1H-indol-3-yl]acetic acid,
(1-isopropyl-2-methyl-1H-pyrrole[2,3-b]pyridin-3-yl)acetic acid, and
(3-benzoyl-2-methoxyphenyl)acetic acid.

4. The method of claim 1, in which the compound of the formula (I) is administered in a dose from 1 to 1500 mg/day.

* * * * *